US007485293B1

United States Patent
Faustman

(10) Patent No.: US 7,485,293 B1
(45) Date of Patent: Feb. 3, 2009

(54) METHOD FOR INHIBITING TRANSPLANT REJECTION

(76) Inventor: Denise L. Faustman, 74 Pinecroft Rd., Weston, MA (US) 02193

( * ) Notice: Subject to any disclaimer, the term of this patent is extended or adjusted under 35 U.S.C. 154(b) by 865 days.

(21) Appl. No.: 09/913,664

(22) PCT Filed: Feb. 18, 2000

(86) PCT No.: PCT/US00/04270

§ 371 (c)(1), (2), (4) Date: Aug. 17, 2001

(87) PCT Pub. No.: WO00/48462

PCT Pub. Date: Aug. 24, 2000

Related U.S. Application Data

(63) Continuation-in-part of application No. 09/252,331, filed on Feb. 18, 1999, now abandoned.

(51) Int. Cl.
*C12N 5/08* (2006.01)
*C12N 5/06* (2006.01)
*A01N 63/00* (2006.01)

(52) U.S. Cl. .................. 424/93.7; 435/325; 435/366

(58) Field of Classification Search .................. 435/1.1, 435/2, 325, 381
See application file for complete search history.

(56) References Cited

U.S. PATENT DOCUMENTS

| 4,383,832 | A | | 5/1983 | Fraefel et al. |
| 4,399,123 | A | | 8/1983 | Oliver et al. |
| 5,081,030 | A | * | 1/1992 | Civin .......................... 435/380 |
| 5,283,058 | A | | 2/1994 | Faustman |
| 5,397,353 | A | * | 3/1995 | Oliver et al. |
| 5,413,923 | A | | 5/1995 | Kucherlapati et al. |
| 5,416,260 | A | | 5/1995 | Koller et al. |
| 5,670,358 | A | * | 9/1997 | Lee et al. ..................... 435/212 |
| 6,110,206 | A | * | 8/2000 | Stone ....................... 623/13.11 |
| 6,156,306 | A | * | 12/2000 | Brownlee et al. ......... 424/93.21 |
| 6,322,593 | B1 | * | 11/2001 | Pathak et al. .............. 623/23.72 |
| 6,617,171 | B2 | * | 9/2003 | Faustman et al. ........... 436/506 |

FOREIGN PATENT DOCUMENTS

| EP | 0 664 337 A1 | 7/1995 |
| WO | WO 94/16065 | 7/1994 |
| WO | WO 97/08328 | 3/1997 |
| WO | WO 00/38708 | 7/2000 |

OTHER PUBLICATIONS

Gallaghet et al. Clinical and Experimental Immunology (Oct. 1986) 666 (1) 118-125.*
Abbas et al. Cellular and Molecular Immunology. 5th edition (2003), pp. 78-80.*
Arnon, *Methods in Enzymology*, 19: 226-244 (1970).
Ashton-Rickardt et al., *Cell*, 76: 651-663 (1994).
Bellelli et al., *Invasion Metastasis*, 10:142-169 (1990).
Coffman et al., *The Journal of Immunology*, 151: 425-435 (1993).
Distler and Jourdian, *The Journal of Biological Chemistry*, 248: 6772-6780 (1973).
Faustman and Coe, *Science*, 252: 1700-1702 (1991).
Galati et al., *Cytometry*, 27: 77-83 (1997).
Goldstein, *Transfusion Medicine Reviews*, 3: 206-212 (1989).
Graff et al., *Transplantation*, 4: 425-437 (1966).
Green, *Microbiology Immunology*, 47: 321-330 (1989).
Hogquist et al., *Cell*, 76: 17-27 (1994).
Janeway, Jr., *Immunity*, 1: 3-6 (1994).
Klein et al., *Transplantation*, 22: 384-390 (1976).
Lafferty et al., *Science*, 188: 259-261 (1975).
Lehmann et al., *Nephrol Dial Transplant*, 11: 953-955 (1996).
Li and Faustman, *Transplantation*, 55: 940-946 (1993).
Low, *Biochem, J.*, 244: 1-13 (1987).
Markmann et al., *Transplantation*, 54: 1085-1089 (1992).
Sandrin et al., *Proc. Natl. Acad. Sci. USA*, 90:11391-11395 (1993).
Sebzda et al., *Science*, 263: 1615-1618 (1994).
Sigmon, *Journal of Clinical Apheresis*, 7: 158-162 (1992).
Snell, *Annual Review of Microbiology*, 2: 439-457 (1957).
Stock et al., *Journal of Surgical Research*, 46: 317-321 (1989).
Stockell and Smith, *J. Biol. Chem.*, 227: 1-26 (1956).
Stone et al., *Transplantation*, 65: 1577-1583 (1998).
Watkins et al., *Transplantation Proceedings*, 23: 360-364 (1991).
Sumimoto et al., *Transplantation Proceedings*, 23(3): 2012-2016 (1991).
Wiman et al., *Biochemistry*, 21: 5351-5358 (1982).

* cited by examiner

*Primary Examiner*—Vera Afremova
(74) *Attorney, Agent, or Firm*—Leon R. Yankwich; David G. O'Brien; Yankwich & Associates, P.C.

(57) ABSTRACT

A method for inhibiting rejection of tissues transplanted into a mammalian host is disclosed. Treatment of the tissues with an enzyme or combination of enzyme, particularly papain, to eliminate cell surface structures necessary for recognition by the host's immune system, particularly MHC Class I molecules, avoids or reduces the attack of the host's immune system on the transplanted tissues. Tissues that are enzymatically shaved of MHC Class I antigens and/or other critical adhesion molecules can be rendered at least temporarily resistant or immune to attack by cytolytic T lymphocytes, helper T lymphocytes, antibodies, or other effector cells of a host's immune system, thereby enhancing the survivability of the tissues in the host after transplant.

22 Claims, No Drawings

METHOD FOR INHIBITING TRANSPLANT REJECTION

CROSS-REFERENCE TO RELATED APPLICATIONS

This application is a U.S. national stage filing under 35 U.S.C. § 371 of international application No. PCT/US00/04270, filed Feb. 18, 2000, designating the United States, which is a continuation-in-part of and claims priority to U.S. application Ser. No. 09/252,331, filed Feb. 18, 1999, abandoned.

FIELD OF THE INVENTION

The present invention relates to the avoidance of undesirable immune responses. More particularly, the invention provides a novel means for reducing or eliminating, at least temporarily, the susceptibility of transplanted (donor) tissues to immune-mediated attack by the host's immune system.

BACKGROUND OF THE INVENTION

The immune system of vertebrates has developed an exquisite mechanism to detect and eliminate cells within the body that have become infected by viruses. Viral proteins being produced within the infected cells are broken down into peptides by intracellular proteolytic enzymes. Some of the peptides are enfolded by a particular class (Class I) of proteins of the major histocompatability complex (MHC) of genes and are transported to the cell surface, where the viral peptide/MHC protein complex is displayed as a surface antigen. Circulating cytotoxic T lymphocytes (CTLs) having the appropriate specificity recognize the displayed MHC Class I antigen as foreign and proceed, through activation and a complex lytic cascade, to kill the infected cell.

The MHC Class I proteins are expressed in essentially all nucleated cells of the body and are a key element in the immune system's ability to distinguish between "self" molecules and "foreign" (non-self) molecules. They can be distinguished from the other class of proteins of the major histocompatability complex of genes, known as MHC Class II proteins. In humans, the MHC proteins are also known as HLA (human lymphocyte antigen) proteins; in mice the MHC proteins are also known as H-2 proteins.

The MHC Class II proteins are expressed only on certain of the cells of the immune system, including antigen presenting cells (APCs), some macrophages, follicular dendritic cells and many T and B lymphocytes. Unlike Class I proteins, the MHC Class II proteins become associated with peptides that come from materials outside the cytosolic compartment of the cell. For example, when a macrophage engulfs a bacterium it remains in a vesicle, where the bacterial proteins are broken down into peptides, which peptides bind to Class II proteins to form an antigen complex which migrates to the cell surface, to be exposed to the other components of the immune system.

Although MHC Class I antigens are a magnificent mechanism for combating infection, they also are primarily responsible for the failure of tissues, e.g., cells, organs, or parts of organs, that are transplanted from one mammal (donor) to another (host). This rejection of tissue by the host organism was first observed in mouse skin graft experiments in the 1950s and was named the transplantation reaction. The search for the factor on donor cells that was evidently recognized and attacked by the host's immune system led finally to the characterization of the two classes of MHC proteins. See, Snell, G. D., Ann. Rev. Microbiol., 2:439-57 (1957).

Recognition of donor MHC Class I antigens as foreign (non-self) by host CTLs occurs not only where the donor tissue is from a different species (a xenogeneic transplant) but also where the tissues are from a donor of the same species as the host (an allogeneic transplant). The specificity of the T cell receptors on CTLs and other T cells that bind to MHC Class I and Class II antigens is such that a single amino acid difference in the structure of a MHC antigen can be detected as foreign, leading to an immune response. The MHC proteins are expressed from (a) distinct DNA segments (i.e., multiple Class I and Class II genes) and (b) highly polymorphic gene segments with great diversity in the intrinsic coding sequences, which leads to a high degree of polymorphism in MHC proteins. Thus, between genetically unrelated individuals the incidence of MHC proteins matching is only about 1 in 40,000, and the transplantation reaction is only avoided in the case of isogeneic grafts, i.e., the transplantation of tissues between idividuals having a high degree of genetic identity, such as between identical twins or from a parent to first generation offspring. See, Roitt et al., Immunology (2nd ed. 1989), Chapt. 24, pp. 24.1-24.10.

Several methods have been devised to try and overcome the mechanism of MHC Class I antigen recognition and its consequences for the transplanted tissue. Immunosuppressive drugs such as cyclosporin A are employed to block the activation of T cells after binding between the T cell receptor and the MHC antigen has taken place. Another approach to avoiding transplant rejection, known as perfusion, seeks to decoy the components of the immune system that would react with the donor tissue. This approach may be particularly useful for addressing antibodies capable of reacting with foreign-appearing donor tissue. Prior to transplant, tissue from the donor is introduced into the host; the host's immune system recognizes the donor tissue as foreign and T cell proliferation and antibody production ensue; the decoy donor tissue is destroyed, but the host's immune system is thereby partially depleted of cells and proteins, especially antibodies, that are capable of reacting with donor tissue; thereafter, the transplant tissue from the donor is introduced, at a point where the host's ability to react against the donor tissue is reduced. See, e.g., Watkins et al., Transplantation Proceedings, 23(1):360-4 (1991). Another approach to inhibit T cell recognition of donor tissues is to mask the MHC Class I antigens, or block the binding interaction between the antigens and T cells, for example with monoclonal antibodies against the MHC Class I antigens or with soluble ligands of the T cell receptors of that subpopulation T cells that are capable of recognizing the antigens presented on the donor tissue. See, e.g., U.S. Pat. No. 5,283,058 (Feb. 1, 1994). A variation of this approach is to prepare donor tissues in transgenic animals that have been genetically altered to have decreased or eliminated MHC Class I expression. See, Li et al., Transplantation, 55:940-6 (1993); Coffman et al., J. Immunol., 151:425-35 (1993).

Each of these methods can be effective in overcoming rejection or prolonging the survival of donor tissues, but they also have potential drawbacks. Immunosuppressant drugs can lead to serious side effects such as renal failure and hypertension, and they leave the host open to infection and tumor growth that is ordinarily checked by an operating immune system. Use of perfusion, MHC antigen masking, and transgenic donor animals leaves the uninvolved segments of the host's immune system in place, but these methods can be labor intensive (e.g., in the systematic and selective elimination of host antibodies or T cells, in the preparation of specific, individualized antibodies for masking, or in husbandry of transgenic animal donors); and in addition these methods involve tailoring the preparation of donor tissues to overcome the capabilities of the host's individual immune system, that is, they involve the preparation of materials which in general are species and host restricted and are not interchangeable between different hosts.

The present invention seeks to provide a simpler and more flexible alternative to inhibiting the rejection of transplanted tissues mediated by recognition of donor antigens.

SUMMARY OF THE INVENTION

A method is provided herein for inhibiting rejection by a host of transplanted allogeneic or xenogeneic tissue comprising treating the transplant (donor) tissue with an enzyme capable of cleaving antigenic structures expressed on the cells of the donor tissue. The antigenic structures can be, for example, donor MHC Class I antigens. Removal of MHC Class I antigens from the donor tissue will attenuate the extent of the immune response mounted by the host mammal receiving the transplant. Furthermore, the enzyme treatment is an effective preparatory treatment for all tissues intended for transplant, without regard to the specific MHC antigens displayed on the donor tissue or the specificities of the immune system cells of the host. Papain is the most preferred enzyme for treatment of donor tissue for removal of MHC class I antigens.

The invention provides a method of treating tissues to render them suitable for transplant which comprises treating the donor tissue with an enzyme capable of cleaving MHC Class I antigens, e.g., in an amount and for a sufficient period to remove sufficient MHC Class I antigens to significantly attenuate the host's immune response to the donor tissue, in comparison to the host's immune response to untreated donor tissue. Preferably the mean cell density of MHC Class I antigens will be reduced by over 50%, preferably by over 75%, and most preferably by over 95% compared to untreated tissue.

In a preferred method, tissue destined for transplant is treated with papain.

The invention also provides treated mammalian tissue suitable for use in transplantation which has been at least partially denuded or shaved of MHC Class I antigens by treatment with an enzyme, most preferably papain.

DESCRIPTION OF THE PREFERRED EMBODIMENTS

The tissues that are advantageously treated in accordance with the teachings herein can be any tissues of benefit to a host in need of such tissues. The tissues can be cells, e.g., blood cells, epithelial cells, insulin-secreting islet of Langerhans cells, myoblasts, cardiac cells, fibroblasts, liver cells, neurons, skin cells, blood cells, precursor lineage cells, genetically engineered cells, or bone marrow cells, or the tissues can be organs, e.g., heart, lung, liver, kidney, brain, or can be part of an organ, e.g., heart or other muscle tissue, sections of intestine or blood vessels, skin, etc. The donor tissue can be xenogeneic or allogeneic with respect to the host.

The enzyme selected for use in this method must be capable of cleaving MHC Class I antigens, that is, removing a MHC Class I protein/peptide complex from the surface of a cell on which it is displayed. Any cleavage that alters the MHC Class I antigen as displayed sufficiently to avoid interaction with the immune system cells of the host is suitable, however preferably substantially all of the extracellular portion of the MHC Class I antigen will be removed from the cell. Any amount of MHC Class I antigen that can be removed from the donor tissue will be helpful in avoiding rejection of the transplant, however preferably the presence of antigens on the donor tissue will be diminished to the point where the immune response of the host is altered in comparison to the response mounted against untreated tissue. As a practical matter, removal of as much of the MHC Class I antigens as possible without killing the tissue is desired. Preferably the mean MHC Class I density on the treated cell is reduced below 5.0, more preferably below 3.0, most preferably below 2.0, as measured by flow cytometry using a fluorescently labeled anti-MHC Class I antibody. In comparative terms, the amount of MHC Class I antigen on the surface of the donor tissue cells will be reduced by over 50%, more preferably by over 75%, and most preferably by over 95%.

The tissues intended for transplant are contacted with the enzyme at a sufficient concentration and for a sufficient period to effect removal of Class I antigens. Conveniently this can be accomplished by bathing the donor tissue in a solution of the enzyme for a period to allow the enzyme to react with the MHC proteins, e.g., from 5 minutes to 24 hours or more. At high enzyme concentration, incubation of tissues may be for even shorter periods, so long as the cells of the tissues are not damaged. Since the tissues must remain viable after transplant, the treatment must be adjusted so that not too great a percentage of the donor cells are killed during the treatment process or otherwise rendered unsuitable for transplantation. In general, at least 75% viability of the tissue cells is sought. Preferably more than 90% of the cells of the tissue will remain viable after the enzyme treatment. The enzyme treatment may be carried out at room temperature (e.g., about 22° C.) or low temperature, for example at 4° C., but most preferably the temperature of the treatment will be at or near the normal body temperature of the donor or the host, for example, 37° C.

There are several advantages to the use of enzymes as a treatment for avoiding transplant rejection; (a) the enzymes are comparatively inexpensive, many are commercially available in high purity with well-characterized activity and specificity; (b) the enzyme reagents are in most cases very stable and can be stored for months without special handling or refrigeration; (c) enzymes can be used locally or in vitro to avoid systemic treatments; (d) the effectiveness of the enzyme treatment does not depend on permanent or constant attachment or binding to donor cell surface structures, thus decreasing untinentional opsonization of the donor tissue; (e) enzyme shaving of the transplant tissue can be used in combination with (i.e., without foreclosing) other complementary treatments or therapies; and (f) the use of enzymes is not species-restricted or allelically restricted, and thus the method is adaptable to veterinary, human and xenogeneic tissue treatment without radical modification of the procedures or reagents. Since the tissues will remain viable after treatment according to this invention, expression of MHC molecules will continue, and eventually reappearance of MHC antigens on the donor tissue will occur, e.g., after transplantation; consequently, it is contemplated that the present method will be used as part of an overall therapy that may include additional measures to avoid latent rejection, such as immunosuppression, plasmaphoresis, antigen blocking, transfection, tolerance induction in the host by the early masking of the donor graft, and the like.

Reappearance of MHC antigens may be used to advantage for inducing tolerance of the donor graft, through re-education of the recipient's immune system to recognize and tolerate the donor antigens as they reappear. Serial grafts from the same donor are contemplated for "pre-tolerization" of a recipient, e.g., by first infusing syngeneic or isogeneic donor lymphocytes or other tissues treated according to this invention, which regenerate donor MHC antigens that are exposed to the recipient's immune system, after which a secondary transplant of donor tissue (treated or untreated) can be made to a recipient that is now tolerant of the donor graft.

Although pre-transplantation treatment of the tissues will be the most common practice, it is also contemplated that the method of the present invention will be employed in situ to effect local immune response inhibition to preserve previously transplanted tissue. In such cases, cleavage of the surface antigen produces a local, soluble, competitive receptor for the cells of the host's immune system, which may serve to effectively blunt immune attack on the transplant.

Any enzyme that is capable of cleaving MHC Class I proteins is suitable for use in the method of this invention. Useful enzymes include proteolytic enzymes, glycosidases, proteinases and combinations of such enzymes that may sufficiently alter the surface antigens to inhibit subsequent transplant rejection. Examples include endoproteinase, pepsin, papain, chymotrysin, trypsin, collagenase, cyanogen bromide, enterokinase (Asp or Glu-specific), iodosobenzoate, lysobacter endoproteinase, proleases, N-bromosuccinimide, N-chlorosuccinimide, hydroxylamine, 2-nitro-5-thiocyanobenzoate, endopeptidase, and the like.

The preferred reagent for use in the method of this invention is papain. Papain is known to cut all MHC Class I molecules of different alleles and different species in the α3 domain, which is exposed on the cell surface. Papain does not cut the α1 or α2 domains.

Papain cutting characteristics are well described. Papain is the major ingredient of meat tenderizers and is a sulfhydryl protease isolated from the latex of the green fruit of papaya. It was first isolated in 1955 and its enzymatic capabilities have been extensively documented. In its native state, the enzyme is inactive, and therefore donor tissue treatments may be advantageously carried out with a high degree of control, using native papain in the presence of activators such as cysteine (0.005M) and/or EDTA (0.002M). See, generally, Arnon, R., *Methods in Enzymology*, 19:226-244 (1970); Stockell et al., *J. Biol. Chem.* 227:1-26 (1957).

The present invention is especially directed to reduction in donor MHC Class I antigens, since the MHC Class I antigens play such a pivotal role in immune recognition and host rejection of the transplanted donor tissue. However, there are many additional surface antigens that play roles in activating the immune system of the host, and enzymatically reducing the level of such additional antigens is specifically contemplated. In preferred embodiments of the present invention, enzyme treatment of donor tissue will include a combination of enzymes, directed at reducing the levels of MHC class I antigens and at least one other surface antigenic structure of the donor tissue.

Other surface antigenic structures that may be addressed according to the present invention include, for example, α-gal (i.e., Gal(α1-3)Gal(β1-4)GlcNAc-R carbohydrate epitopes), which have been observed to mediate hyperacute rejection of xenogeneic transplants; blood group antigens; other lymphocyte surface antigens (e.g., LFA-3, CD2, CD4, CD44, B-7); and any other cell surface structures that mediate a host immune response.

The treatment of the present invention is advantageously carried out by contacting the donor tissue with a solution containing active enzyme(s) under conditions and for a period sufficient to reduce the level of cell surface MHC Class I antigens and any other surface antigenic structures desired to be eliminated or reduced. The exact concentration of enzymes, the duration of contact and other conditions, such as temperature, will be adjusted by the practitioner to optimize the desired results. Any reduction of the donor MHC Class I antigen that results in an attenuated immune response by the host is desirable, and in general the greater the reduction in the surface population of MHC class I antigens present, the more attenuated will be the host immune response. Where more than one enzyme is used, consideration of the optimal cutting conditions and rate of the desired enzymatic reaction for each individual enzyme will determine whether the enzymes are most effectively employed serially or together.

In a preferred embodiment, the donor tissue can be prepared for transplantation by immersion in a bath or solution containing the enzyme(s). For donor cells being prepared for transplant, the enzymes are preferably added to a stirred culture solution. For donor organs, it is preferred to perfuse the organ with a preservative solution, as is well known in the art, and the enzyme(s) to be used according to the invention are advantageously added to this perfusion solution, most preferably directly before transplant. Also, transplantation packs are contemplated for shipment or storage of donor cells, tissues or organs comprising a container enclosing together the donor material with a preservative or nutrient solution for maintaining the viability of the donor material and one or more enzymes, preferably in inactive form, suitable (when activated) for reducing the MHC Class I antigen population on the donor material sufficiently to prolong its survival after transplantation in the host. Alternatively, the donor tissue intended for transplant can be briefly treated immediately prior to transplantation into the host, e.g., in the operating room.

Specific embodiments of the present invention are described in the following examples, which are provided by way of illustration, and not with the intention of limiting the scope of the invention.

EXAMPLE 1

A MHC Class I molecule consists of a transmembrane α-chain having three extracellular domains (α1, α2, α3) and a noncovalently associated polypeptide, $\beta_2$ microglobuline, which helps to stabilize the α-chain on the surface of the cell. Although the most distal α1 and α2 domains are highly polymorphic, the stem of the Class I α-chain (α3 domain) is highly conserved within species and between species.

A computer search of enzyme cleavage sites for MHC Class I revealed a multitude of susceptible cleavage sites by a multitude of enzymes.

To see if papain conditions could be set appropriately for use on viable cells to remove Class I, immortalized human B lymphocytes and H4Tg rat hepatoma cells (ATCC, Manassas, Va., accession nos. CCL-214 and CRL-1578) were treated with varying concentrations of papain. MHC Class I density was analyzed by flow cytometer (Coulter Epics Elite cell sorter) utilizing an anti-MHC Class I antibody directly conjugated to a fluorescent fluorochrome. After treatment, cell viability was also assessed by phase contrast microscopy, with and without Trypan blue staining.

A stock solution of papain was produced at 26.4 mg/ml in RPMI media with 0.01M EDTA and 0.01M β-mercaptoethanol (β-ME). The β-mercaptoethanol stock was 1.12 g/ml (14.3M) and for a 1M stock, 0.1M stock was added to 1.33 ml of RPMI. A total 10 ml final reagent of media with papain was produced from 9.7 ml media plus 0.2 ml of 0.5 M EDTA and 0.1 ml 1M β-mercaptoethanol. Therefore, the final concentration of EDTA was 0.01M; the final concentration of β-mercaptoethanol was 0.01M.

The human B cells were incubated with papain and the media reagent for 60 minutes at 37° C. The following groups were tested:

| Group | Treatment |
|---|---|
| 1. | 0.2 ml papain and 0.8 ml media |
| 2. | 0.02 ml papain and 0.8 ml media |
| 3. | 0.002 ml papain and 0.8 ml media |
| 4. | 0.2 ml papain and 0.8 ml media |
| 5. | No papain and 0.8 ml media |
| 6. | No papain, 0.8 ml media and no fluorescent reagent (checked for background, autofluorescence) |

| Group | Mean MHC Class I density, per cell | Viability |
|---|---|---|
| 1. | 1.8 | >90% |
| 2. | 5.6 | >90% |
| 3. | 15.6 | >90% |
| 4. | 2.6 | >90% |
| 5. | 18.1 | >90% |
| 6. | 1.9 | >90% |

Papain treatment of human B cells resulted in essentially complete removal of MHC Class I under the described conditions above and allowed the cells to remain viable beyond 4 hours after treatment.

EXAMPLE 2

Rat hepatoma cells (ATCC, Manassas, Va., accession no. CRL-1578) were treated under the same papain conditions described above, with 0.2 ml papain solution and 0.8 ml media reagent for transplantation into C57BL/6 mice (n=10 test mice; n=20 control mice), in order to investigate the possibility of enhanced xenograft survival by the removal of MHC Class I with papain. The host mice were non-immunosuppressed. The transplants were evaluated for survival at 30 days.

After one hour of papain treatment, the treated liver cells were immediately transplanted under the kidney capsule by syringe injection. Control mice received untreated liver cells. Approximately $5 \times 10^6$ liver cells were injected per mouse. At 30 days post-transplantation, the mice were sacrificed by cervical dislocation. The kidney receiving the transplant was placed in fixative for histologic evaluation.

In the control group, individual control mice were sacrificed each day for ten days and the kidney capsules examined histologically to determine the fate of the transplanted cells. It was determined that unmodified xenogeneic cells were rapidly and uniformly rejected within 3-5 days after transplantation. In contrast, at thirty days post-transplant, 9 of the 10 mice receiving treated donor cells had surviving rat hepatoma cells under the kidney capsule.

EXAMPLE 3

The use of porcine organs for xenografts has often been limited because of hyperacute rejection episodes attributed to preformed host antibodies that are reactive with carbohydrate structures on the donor tissue (i.e., α-gal).

FITC-conjugated lectin (IB4, Sigma Chemical Co., St. Louis, Mo.) reacts with Gal(α1-3)Gal-linked sugars and thus vividly binds to pig cells. Human antibodies also bind to these carbohydrate structures and therefore compete with the lectin for the binding site.

Porcine blood cells obtained from a slaughterhouse were made resistant to preformed human antibodies in a blood sample from a single human donor with negative history of organ transplant by treatment with a commercially available α-galactosidase at pH 7.3, 37° C. for 45 minutes. This treatment totally prevented lectin binding. This experiment was repeated four times with similar results.

| Immunofluorescence Intensity of Lectin Binding to Pig Cells | | |
|---|---|---|
| First Reagent | Second Reagent | Fluorescence Intensity |
| 1. Lectin-FITC | 0 | ++++ |
| 2. Human Serum 1:20 | Lectin-FITC | 0 |
| 3. Human Serum 1:100 | Lectin-FITC | 0 |
| 4. Human Serum 1:1,000 | Lectin-FITC | 0 |
| 5. Human Serum 1:10,000 | Lectin-FITC | + |
| 6. Human Serum 1:50,000 | Lectin-FITC | ++ |
| 7. α-galactosidase | Lectin-FITC | 0 |

Approximately $1 \times 10^6$ pig RBC were incubated with 500 g of media with or without lectin, human serum or α-galactosidase, as in the chart above. Cell survival and cell viability were assessed after each treatment and no difference existed between the groups. The lectin was at a concentration of 300 mM. The α-galactosidase was purchased from Sigma (St. Louis, Mo.) at approximately 0.15 unit per mg protein at pH 7.3 at 37° C.

EXAMPLE 4

Porcine lymphocytes were treated to remove both MHC Class I and α-gal antigenic structures, in order to determine the effect on reactivity with human serum.

Approximately $1 \times 10^6$ porcine lymphocytes in each group were treated as follows:

| Group | Treatment |
|---|---|
| 1. | no enzyme treatment |
| 2. | 0.15 U/mg α-galactosidase at pH 7.3, 37° C. |
| 3. | 0.2 ml papain and 0.8 ml media (.01 M EDTA, .01 M β-ME), 1 hour, 37° C. |
| 4. | α-galactosidase treatments as in group 2, wash 2× with Hanks medium + 5% albumin then treatment with papain as in group 3 |

The porcine lymphocytes from each group were mixed with human serum for 45 minutes at 37° C. from a single human donor with a negative history for transplant and tested with two reagents, FITC-conjugated anti-MHC Class I antibody (W6/32, Accurate Chemical, Westbury, N.Y.) or FITC-conjugated lectin (Sigma). The results appear below:

| Group | W6/32 binding | lectin binding |
|---|---|---|
| 1. | ++++ | ++++ |
| 2. | +++++ | + |
| 3. | + | ++++ |
| 4. | +/0 | + |

The foregoing results show that with sequential incubations with more than one enzyme, it is possible to decrease both MHC Class I and α-gal and reduce the reactivity of the porcine cells to components of human serum.

OTHER EMBODIMENTS

Although removal of MHC Class I antigens has been specifically described, there are many cell-cell interactions that may be undesirable, not only in the context of transplant rejection but also in infection, conception, inflammation, allergy, and many other physiological phenomena. For example, the activation of CTLs touching off the lytic cascade that leads to the transplantation reaction, not only involves binding of the CTL T cell receptor with the MHC Class I antigen of the target cell but also involves reciprocal interation of CD8 with the MHC Class I proteins, CD2 with LFA-3, and LPA-1 with ICAM-1. See, e.g., Faustman et al., *Science*, 252:1700-2 (1991). Shaving of surface LFA-3 and/or ICAM-1, or surface adhesion molecules involved with other pathways than the cytolytic pathway, may also be accomplished following the principles of this disclosure, thereby heading off additional avenues of immune attack, or other undesirable cell-cell interactions.

After analysis of the known target structures, many well-characterized enzymes will be available for removal or alteration of the structures so as to attenuate the reactivity of the structures with its natural receptor(s).

Additional such enzymatic reagents will include oxidoreductases acting on: (1) OH—OH groups; (2) aldehyde or keto groups; (3) CH—CH groups; (4) CH—$NH_2$ groups; (5) reduced AND or NADP; (6) nitrogenous compounds; (7) diphenols; (8) acting on $H_2O$; (9) hydrogen; (10) acting on single donors with incorporation of oxygen; and (11) acting on paired donors with incorporation of oxygen into one donor; transferases: (1) transferring one-carbon groups (methyltransferase, hydroxymethyl-, formyl- and related transferases, carboxyl- and carbarnoyltransferases, amidinotransferases); (2) transferring aldehydic or ketonic residues; (3) acting on acyltransferases (acyltransferases, aminoacyltransferases); (4) acting on glycosyltransferases (hexosyltransferases, pentosyltransferases); (5) transferring alkyl or related groups; (6) transferring nitrogenous groups; (7) transferring phosphorus-containing groups (phosphotransferases with an alcohol group as acceptor, phosphotransferases with a carboxyl group as acceptor, phosphotransferases with a nitrogenous group as acceptor, phosphotransferases with a phosphate group as acceptor, phosphortransferases, pyrophosphotransferases,, nucleotidyltransferases, transferases for other substituted phospho- groups); and, (8) transferring sulfur-containing groups (sulfurtransferases, sulfotransferases, CoA-transferases); hydrolases: (1) acting on ester bonds (carboxylic ester hydrolases, thiolester hydrolases, phosphoric monoester hydrolases, phosphoric diester hydrolases, triphosphoric monoester hydrolases, sulfuric esterhydrolases); (2) acting on glycosyl compounds (glycoside hydrlases, hydrolysing N-glycosyl compounds, Hydrolysing S-glycosyl compounds); (3) acting on either bonds (thioether hydrolases); (4) acting on peptide bonds (peptide hydrolases) (α-amino-acyl-peptide hydrolases, peptidyl-amino-acid hydrolases, dipeptide hydrolases, peptidyl-peptide hydrolases); (5) acting on C—N bonds other than peptide bonds (in linear amides, in cyclic amides, in linear amidines, in cyclic amidines, in cyanides); (6) acting on acid-anhydride bonds (in phosphoryl-containing anhydrides); (7) acting on C=C bonds; (8) acting on carbon-halogen bonds; (9) acting on P—N bonds; lyases (1) acting on carbon-carbon bonds (carboxyl-lyases, aldehyde-lyases, keto acid-lyases); (2) acting on carbon-oxygen bonds (hydrolyases and other carbon-oxygen lyases); (3) acting on carbon-nitrogen bonds (amonialyases and amidine-lyases); (4) carbon-sulfur lyases; (5) carbon-halogen lyases; (6) other lyases; isomerases: (1) racemases and epimerases (acting on amino acids and derivatives; acting on hydoxyacids and derivatives, acting on carbohydrates and derivatives, acting on other compounds); (2) acting on cis-trans isomerases; (3) acting on intramolecular oxidoreductases (interoconverting aldoses and ketoses, interconverting keto- and enol-groups, transposing C=C bonds); (4) acting on intramolecular transferases (transferring acyl groups, transferring phosphoryl groups, transferring other groups); (5) acting on intramolecular lyases; (6) other isomerases; ligases: (1) acting on forming C—O bonds (amino-acid-RNA ligases); (2) acting on forming C—N bonds (acid-ammonia ligases (amide synthetases), acid-amino-acid ligases (peptide synthetases), cyclo-ligases, other C—N ligases, C—N ligases with glutamine as N-donor); (3) forming C—C bonds; and glycosidases, such as α-mylase, β-amylase, glucoamylase, celulase, laminarinase, inulase, dextranase, chitinase, polygalacturonase, lysozyme, neuraminidase, α-glucosidase, β-glucosidase, α-galactosidase, β-galactosidase, α-mannosidase, β-fructofuranosidase, trehalase, chitobiase, β-acetylglucosaminidase, β-glucuronidase, dextrin-1,6-glucosidase, hyaluronidase, β-D-fucosidase, metalopeptidases and nucleosidase.

The publications cited above are incorporated herein by reference. Additional embodiments of the present invention will be apparent from the foregoing disclosure and are intended to be encompassed by the invention as described fully herein and defined in the following claims.

What is claimed is:

1. A method for inhibiting rejection by a host mammal of donor tissue from another mammal which is transplanted into the host mammal, said method comprising
    (a) treating viable donor tissue with an enzyme effective for temporarily ablating MHC Class I antigens from said donor tissue,
    (b) transplanting said treated, viable donor tissue into said host mammal before MHC Class I antigens are re-expressed on the surface of said donor tissue, and
    (c) maintaining said viable donor tissue in said host.

2. The method according to claim 1, wherein said donor tissue is from a mammal that is the same species as said host mammal.

3. The method according to claim 1, wherein said donor tissue is from a mammal that is of a different species than said host mammal.

4. The method according to claim 1, wherein said host mammal is a human.

5. The method according to claim 1, wherein said tissue comprises blood cells, neurons, hepatocytes, cardiac cells, genetically modified cells, skin cells, precursor cells, endothelial cells, fibroblasts, myoblasts, islets of Langerhans cells, or bone marrow cells.

6. The method according to claim 1, wherein said tissue is an organ or part of an organ.

7. The method according to claim 6, wherein said organ is selected from the group consisting of skin, kidney, heart, pancreas, brain, and liver.

8. The method according to claim 1, wherein said donor tissue is additionally treated with a second enzyme effective to remove an antigenic surface structure from said donor tissue.

9. The method according to claim 1, wherein said enzyme is papain.

10. The method according to claim 8, wherein said second enzyme is α-galactosidase.

11. The method according to claim 8, wherein said donor tissue is treated with a combination of papain and α-galactosidase.

12. A method for inhibiting rejection by a host mammal of donor tissue from another mammal which is transplanted into the host mammal, said method comprising:
(a) treating a first viable donor tissue with an enzyme effective for temporarily ablating MHC Class I antigens from said donor tissue,
(b) transplanting said treated, viable donor tissue into said host mammal before MHC Class I antigens are re-expressed on the surface of said donor tissue, and
(c) maintaining said viable donor tissue in said host mammal, and
(d) transplanting a second donor tissue into said host mammal.

13. The method according to claim 12, wherein said first donor tissue is donor lymphocytes.

14. The method according to claim 12, wherein said second donor tissue is also treated prior to transplantation with an enzyme effective for removing MHC Class I antigens from said tissue.

15. The method according to claim 12, wherein said first and second donor tissue is from a mammal that is the same species as said host mammal.

16. The method according to claim 12, wherein said first and second donor tissue is from a mammal that is of a different species than said host mammal.

17. The method according to claim 12, wherein said host mammal is a human.

18. The method according to claim 12, wherein said first and second donor tissue independently comprises blood cells, neurons, hepatocytes, cardiac cells, genetically modified cells, skin cells, precursor cells, endothelial cells, fibroblasts, myoblasts, islets of Langerhans cells, or bone marrow cells.

19. The method according to claim 12, wherein said first and second donor tissue is an organ or part of an organ.

20. The method according to claim 19, wherein said organ is selected from the group consisting of skin, kidney, heart, pancreas, brain, and liver.

21. The method according to claim 1, wherein said donor tissue is treated with a solution of papain at 5-60 mg/ml for a period of 5 minutes to 24 hours.

22. The method according to claim 21, wherein said solution contains 20-28 mg/ml papain and said tissue is treated for 30-120 minutes.

* * * * *